(12) United States Patent
Assawah

(10) Patent No.: US 6,440,145 B1
(45) Date of Patent: Aug. 27, 2002

(54) BROAD FACED MEDICAL INSTRUMENT AND ITS ASSOCIATED METHOD OF USE

(76) Inventor: Wagdy A. Assawah, 17 Penn Valley Rd., Apt D-6, Levittown, PA (US) 19054

( * ) Notice: Subject to any disclaimer, the term of this patent is extended or adjusted under 35 U.S.C. 154(b) by 0 days.

(21) Appl. No.: 09/550,633

(22) Filed: Apr. 17, 2000

(51) Int. Cl.[7] ................................. A61B 17/08
(52) U.S. Cl. ................. 606/151; 606/157; 24/514
(58) Field of Search .................. 606/151, 157, 606/216, 221, 50–52, 37, 48; 132/279, 276, 223, 224; 24/514, 569; 269/143, 249; 128/898

(56) References Cited

U.S. PATENT DOCUMENTS 4,832,027 A * 5/1989 Utz ............................ 606/151
6,123,701 A * 9/2000 Nezhat ........................ 606/50

* cited by examiner

*Primary Examiner*—David O. Reip
*Assistant Examiner*—Julian W. Woo
(74) *Attorney, Agent, or Firm*—LaMorte & Associates

(57) ABSTRACT

A medical instrument and its method of use to remove flaps of skin. The medical instrument has the form of a broad faced clamp that has two narrow opposing surfaces. The medical instrument is opened and a flap of skin is placed between the narrow opposing surfaces. The narrow opposing surfaces are biased toward one another with enough force to stop the flow of blood into the flap of skin, The bias between opposing surfaces is maintained over time until the flap of skin dies and withers. Once the flap of skin has died and the blood vessels no longer flow to the flap of skin, the medical instrument is removed. The remaining dead skin is then cut away from the body. The excess flap of skin is therefore removed without ever having produced an open incision that can be contaminated.

12 Claims, 2 Drawing Sheets

BROAD FACED MEDICAL INSTRUMENT AND ITS ASSOCIATED METHOD OF USE

BACKGROUND OF THE INVENTION

1. Field of the Invention

In general, the present invention relates to medical instruments that are used to remove human tissue. More particularly, the present invention relates to medical instruments that isolate areas of tissue so that the isolated tissue areas wither and die.

2. Description of the Prior Art

In the practice of medicine, there are many instances where tissue must be cut and removed from the body. Typically, doctors use two different techniques to remove tissue. The first technique is to use a scalpel. Scalpels have a single cutting edge that is guided by the doctor's hands. The scalpel provides no mechanical advantage to cutting edge. As such, the depth and length of the cut is totally dependent upon the skill of the doctor using the scalpel.

The second most common technique used to cut tissue is to use dissecting scissors. In medicine, dissecting scissors come in a large variety of shapes and sizes. Scissors do provide a mechanical advantage to the cutting edges of the scissors. As such, it is easier for a doctor to cut through tough tissue with a scissor than with a scalpel.

A first disadvantage of both scalpels and scissors is that they are used as part of invasive surgical procedures that leave the body open to contaminants that may cause infection. Furthermore, the wound left by scalpels and scissors must be closed with stitches, stapes or the like until the wound heals closed.

Another disadvantage of both scalpels and scissors is that they have relatively small cutting edges. As such, it a doctor desires to cut away a large area of tissue, the scalpel or scissors must be constantly manipulated to propagate the cut. Very little tissue in the human body if flat or even straight. As such, it is difficult for a doctor to maintain a straight incision when moving a scalpel or scissors across a prolonged length of tissue. To help doctors make straight cuts, doctors often mark the tissue with ink prior to cutting. As such, when the cutting begins, the doctor knows to move the scalpel or scissor along the marked line. Again, great skill is needed to accurately follow the marked line with the limited cutting capabilities of scalpels and scissors.

A need therefore exists in the art for a new medical instrument and method that can be used to removed tissue without ever creating an open wound. A need also exists for dissecting instrument and method that can dissect a long section of tissue in a single cutting process. In this manner, long incisions need not be made by numerous small cuts that require great surgical skill. Rather, a tissue can be removed in a single accurate process, thereby eliminating the need for great skill. These needs are met by the present invention as described and claimed below.

SUMMARY OF THE INVENTION

The present invention is a medical instrument and its method of use to remove flaps of skin. The medical instrument has the form of a broad faced clamp that has two narrow opposing surfaces. The medical instrument is opened and a flap of skin is placed between the narrow opposing surfaces. The narrow opposing surfaces are biased toward one another with enough force to stop the flow of blood into the flap of skin, The bias between opposing surfaces is maintained over time until the flap of skin dies and withers. Once the flap of skin has died and the blood vessels no longer flow to the flap of skin, the medical instrument is removed. The remaining dead skin is then cut away from the body. The excess flap of skin is therefore removed without ever having produced an open incision.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Although the present invention instrument can be used in the dissecting of many different types of tissue, it is particularly well suited for removing flaps of skin from the body. As a result, the exemplary embodiment of the present invention instrument described shows the instrument being used to remove a flap of skin from the human body in order to set forth the best mode contemplated for the invention.

Figure 1:
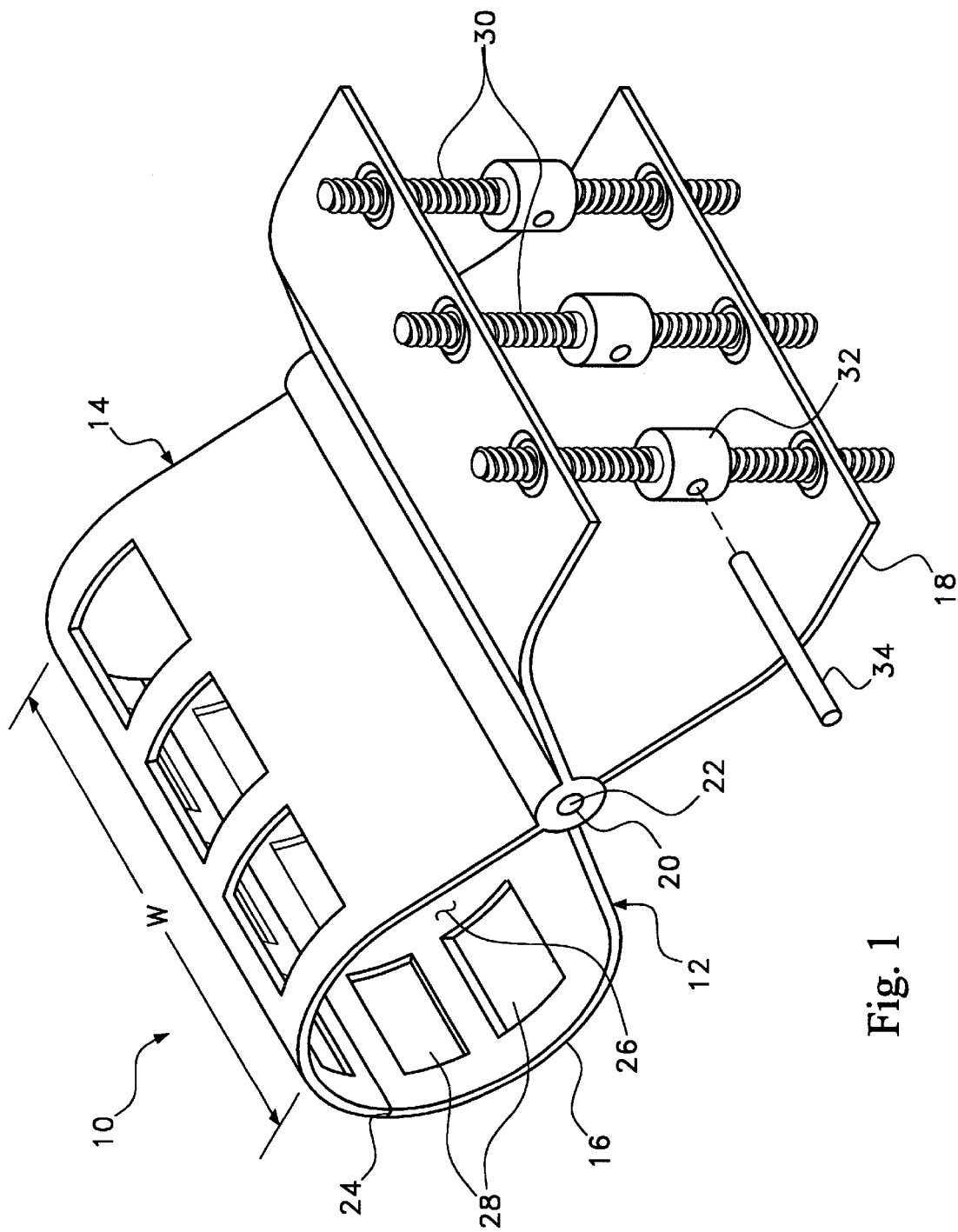
FIG. 1 is a perspective view of an exemplary embodiment of a medical instrument in accordance with the present invention.

Referring to FIG. 1, an exemplary embodiment of the present invention instrument 10 is shown. The instrument 10 has two opposing halves 12, 14. Each half of the instrument is very wide, having a width W that is preferably between three inches and twelve inches. Each half 12, 14 of the instrument 10 is divided into two sections, which are the jaw section 16 and the tail section 18. A pivot aperture 20 is disposed through each half 12, 14 at the junction between the jaw section 16 and the tail section 18. A pivot rod 22 passes through the pivot aperture 20, thereby pivotably connecting the two halves 12, 14. As such, the two jaw halves 16 extend from one side of the pivot and the two tail sections 18 extend from the opposite side of the pivot.

Each jaw section 16 is curved. However, each jaw section 16 has a narrow straight contact edge 24 at one side. The contact edge is preferably less than ¼ inch thick. As such, when the contact edges 24 of the two jaw sections 16 abut against each other, they define an interior space 26. Furthermore, each of the jaw sections 16, preferably contains apertures 28 that extend through the structure of the jaw sections 16. The apertures 28 enable the interior space 26 defined by the jaw sections 16 to be readily viewed from outside the jaw sections 16.

Due to the pivot rod 22 in the pivot aperture 20 on each half of the instrument 10, the contact edges 24 of the jaw sections 16 separate, when the tail sections 18 are bias toward one another. Adversely, when the tail sections 18 of the instrument 10 are biased away from one another, the contact edges 24 of the jaw section 18 become biased against each other.

A plurality of threaded shafts 30 are disposed between the tail sections 18 of the instrument 10. Each threaded shaft 30 has a top section and a bottom section that are threaded with oppositely pitched threads. In the center of each threaded shaft 30 is an turning mechanism 32. The turning mechanism 32 can be a hexagonal nut that can be turned by a wrench. However, in the shown embodiment, the turning mechanism 32 is a element with a bore that is sized to receive a turning rod 34.

Each threaded shaft 30 engages floating nuts (not shown) that are embedded in the tail section 18 of each half of the instrument 10. As such, when the threaded shafts 30 are turned, they either bias the tail sections 18 away from one another or toward one another, depending upon the direction of rotation.

Figure 2:
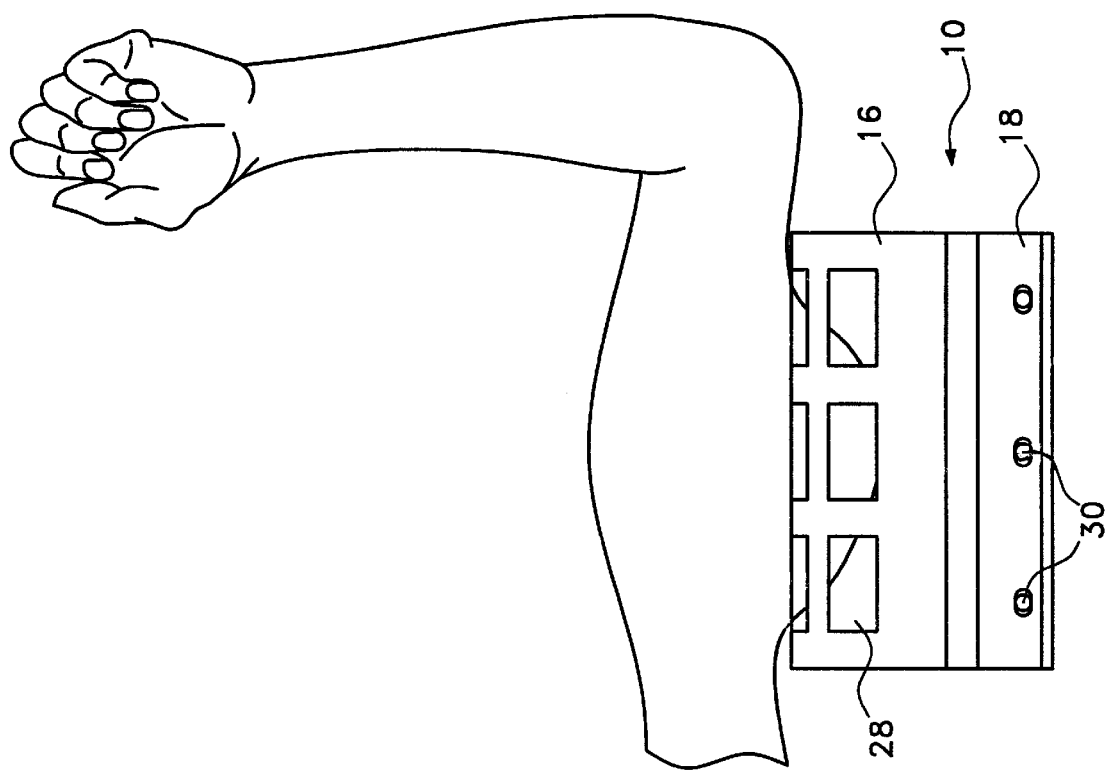
FIG. 2 is a side view of the medical instrument shown in FIG. 1, applied to a flap of skin under a person's arm.

Referring to FIG. 2, an embodiment of the present invention medical instrument 10 is shown attached to the an unwanted fatty skin flap under the arm. The medical instrument 10 is applied by a doctor. To apply the medical instrument 10, the doctor prepares the skin flap by cleaning the skin flap and marking what parts of the skin flap are to be removed. The jaw sections 16 of the instrument are then spread by turning the threaded shafts 30 so that the tail sections 18 of the medical instrument 10 are pulled toward each other. Once opened, the skin flap is placed in between the jaw elements 16 and the jaw elements 16 are tightened toward each other. The threaded shafts 30 are turned in such a way so as to ensure that a continuous, gradual and equally distributed pressure is developed along the contact edges 24 (FIG. 1) of the instrument 10.

As the jaw sections 16 of the medical instrument 10 are closed, the skin flap becomes pinched between the narrow contact edges 24 (FIG. 1) of the jaw elements 16. The skin flap is viewable through the apertures 28 that exist in the jaw sections 28 of the medical instrument 10. The skin flap is clamped upon until the medical instrument 10 stops the flow of blood into the area of the skin flap contained within the medical instrument 10. The jaw sections 16 of the medical instrument 10 can be tightened all at once for thin skin flaps or gradually over time for more fatty skin flaps. The skin flap being removed should not be to protrude beyond the jaw sections 16 of the medical instrument. In this manner, the stoppage of blood flow to the skin flap is ensured.

As blood is prevented from flowing to or from the tissue in the skin flap, the tissue in the skin flap will begin to die and wither. The medical instrument 10, once applied, serves two different functions. The first function is to prevent the flow of blood into and out of the skin flap. The second function is to force the blood capillaries on the other side of the trapped flap to permanently close. As the blood capillaries close, an abscission layer is formed where the pinched skin is forced to meet. This abscission layer will be forged from the crushed cells. Eventually the moribund skin flap separated at the abscission layer, hopefully favoring a seamless bond. However, if it does not, it can be helped with minimal medical intervention. After the medical instrument 30 is removed and the dead skin cut away, the resulting wound is comparable to a healing cut. The time the instrument must remain in place before it can be removed is about ten days in most instances. However, the time needed depends on a multitude of factors. These factors include the size of the skin flap, the thickness of the underlying adipose tissue, the location of the skin flap and heath of the patient.

It will be understood that the embodiments of the present invention described and illustrated herein are merely exemplary and a person skilled in the art can make many variations to the embodiment shown without departing from the scope of the present invention. For example, in the shown embodiment, the jaw sections of the instrument join along a straight line. However, the instrument can be produced so that the jaws join along a curved line so as to be better adapted for use on curved surfaces. All such variations, modifications and alternate embodiments are intended to be included within the scope of the present invention as defined by the appended claims.

What is claimed is:

1. A medical instrument, comprising:
   a first clamping element having a first end and a second end, wherein a first contact edge at least three inches long is disposed at its first end;
   a second clamping element having a first end and a second end, wherein a second contact edge at least three inches long is disposed at its first end and wherein said first clamping element and said second clamping element are pivotably interconnected and said instrument is selectively positionable between an open condition and a closed condition where said first contact edge abuts against said second contact edge; and
   a plurality of threaded shafts disposed between said first clamping element and said second clamping element, wherein said threaded shafts engage said first clamping element and said second clamping element and are capable of biasing said first clamping element and said second clamping element into said closed condition.

2. The medical instrument according to claim 1, wherein said threaded shafts engage said first clamping element and said second clamping element proximate the second end of each element.

3. The medical instrument according to claim 1, wherein said first clamping element has a width equal to said first contact edge.

4. The medical instrument according to claim 3, wherein said second clamping element has a width equal to said second contact edge.

5. The medical instrument according to claim 1, wherein said first clamp element and said second clamp element are joined by a pivot.

6. The medical instrument according to claim 5, wherein said first clamp element and said second clamp element define an internal space between said first contact edge and said pivot when said instrument is in said closed condition.

7. The medical instrument according to claim 6, wherein said first clamping element has apertures formed therethrough that enable said internal space to be viewed through said first clamping element.

8. The medical instrument according to claim 6, wherein said second clamping element has apertures formed therethrough that enable said internal space to be viewed through said second clamping element.

9. The medical instrument according to claim 1, wherein said threaded shafts are linearly aligned and equally spaced in between said first clamping element and said second clamping element.

10. A method of removing a flap of skin from a body, comprising the steps of:
    providing two opposing surfaces;
    placing a flap of skin between the opposing surfaces;
    biasing the opposing surfaces toward one another with enough force to stop blood flow into the flap of skin;
    maintaining the bias between opposing surfaces until the flap of skin dies and withers;
    removing the opposing surfaces from the flap of skin; and
    cutting the flap of skin from the body.

11. The method according to claim 10, wherein said step of biasing the opposing surfaces toward one another includes the substeps of:
    providing a clamp having opposing surfaces that are at least three inches wide; and
    tightening said clamp.

12. The method according to claim 11, wherein said clamp defines a open area behind said opposing surfaces and the skin flap passes into said open area when placed in said clamp.

* * * * *